United States Patent

Tully

(10) Patent No.: US 6,684,526 B2
(45) Date of Patent: Feb. 3, 2004

(54) PROCESS FOR REMOVING TRACE SOLVENT FROM A MATERIAL

(75) Inventor: William Tully, Midleton (IE)

(73) Assignee: Pfizer Science and Technology Ireland, Limited, Dublin (IE)

( * ) Notice: Subject to any disclaimer, the term of this patent is extended or adjusted under 35 U.S.C. 154(b) by 0 days.

(21) Appl. No.: 10/172,617

(22) Filed: Jun. 14, 2002

(65) Prior Publication Data

US 2002/0152629 A1 Oct. 24, 2002

Related U.S. Application Data

(63) Continuation of application No. PCT/IE00/00157, filed on Dec. 18, 2000.

(30) Foreign Application Priority Data

Dec. 17, 1999 (WO) ................................ PCT/IE99/00138

(51) Int. Cl.[7] .............................. F26B 5/04; F26B 11/18
(52) U.S. Cl. .............................. 34/409; 34/443; 34/350; 34/423; 34/192; 34/195; 34/210; 34/237
(58) Field of Search ......................... 34/350, 351, 410, 34/423, 73, 192, 195, 197, 204, 210, 215, 237, 411, 409, 443; 134/26, 30

(56) References Cited

U.S. PATENT DOCUMENTS

| | | | | | |
|---|---|---|---|---|---|
| 2,302,908 | A | * | 11/1942 | Fryer et al. ................... 34/9 |
| 2,634,221 | A | * | 4/1953 | McAlpine et al. ............. 134/9 |
| 3,270,860 | A | * | 9/1966 | Siebach ....................... 198/179 |
| 3,842,515 | A | * | 10/1974 | MacDonald et al. ............. 34/9 |
| 4,745,690 | A | * | 5/1988 | Koop et al. ...................... 34/9 |
| 4,777,970 | A | * | 10/1988 | Kusuhara ..................... 134/66 |
| 4,828,760 | A | * | 5/1989 | Chung et al. ............... 252/627 |
| 5,047,153 | A | * | 9/1991 | Nowak et al. .............. 210/634 |
| 5,364,625 | A | | 11/1994 | Sebag et al. |
| 5,597,830 | A | | 1/1997 | Klohs et al. |
| 5,767,110 | A | | 6/1998 | Klohs et al. |
| 6,045,621 | A | * | 4/2000 | Puri et al. ....................... 134/2 |
| 6,095,167 | A | * | 8/2000 | Florez |
| 6,165,277 | A | * | 12/2000 | Florez .......................... 134/2 |
| 6,286,231 | B1 | * | 9/2001 | Bergman et al. ............. 34/410 |
| 6,289,605 | B1 | * | 9/2001 | Chang .......................... 34/471 |
| 6,357,138 | B2 | * | 3/2002 | Nakabeppu .................... 34/72 |

FOREIGN PATENT DOCUMENTS

GB      224849      4/1925

OTHER PUBLICATIONS

PCT International Search Report for PCT/IE00/00157.
Stein, et al, "Suramin: An Anticancer Drug With a Unique Mechanism of Action", Journal of Clinical Oncology, vol. 7, No. 4 (Apr.), 1989; pp 499–508.

* cited by examiner

Primary Examiner—K. B. Rinehart
(74) Attorney, Agent, or Firm—Francis J. Tinney

(57) ABSTRACT

An improved process for removing trace solvent from a material comprises rewetting the product with water during the drying process. Finished products such as suramin are produced efficiently to a high quality on a factory scale.

36 Claims, 1 Drawing Sheet

PROCESS FOR REMOVING TRACE SOLVENT FROM A MATERIAL

RELATED APPLICATIONS

Figure 1:
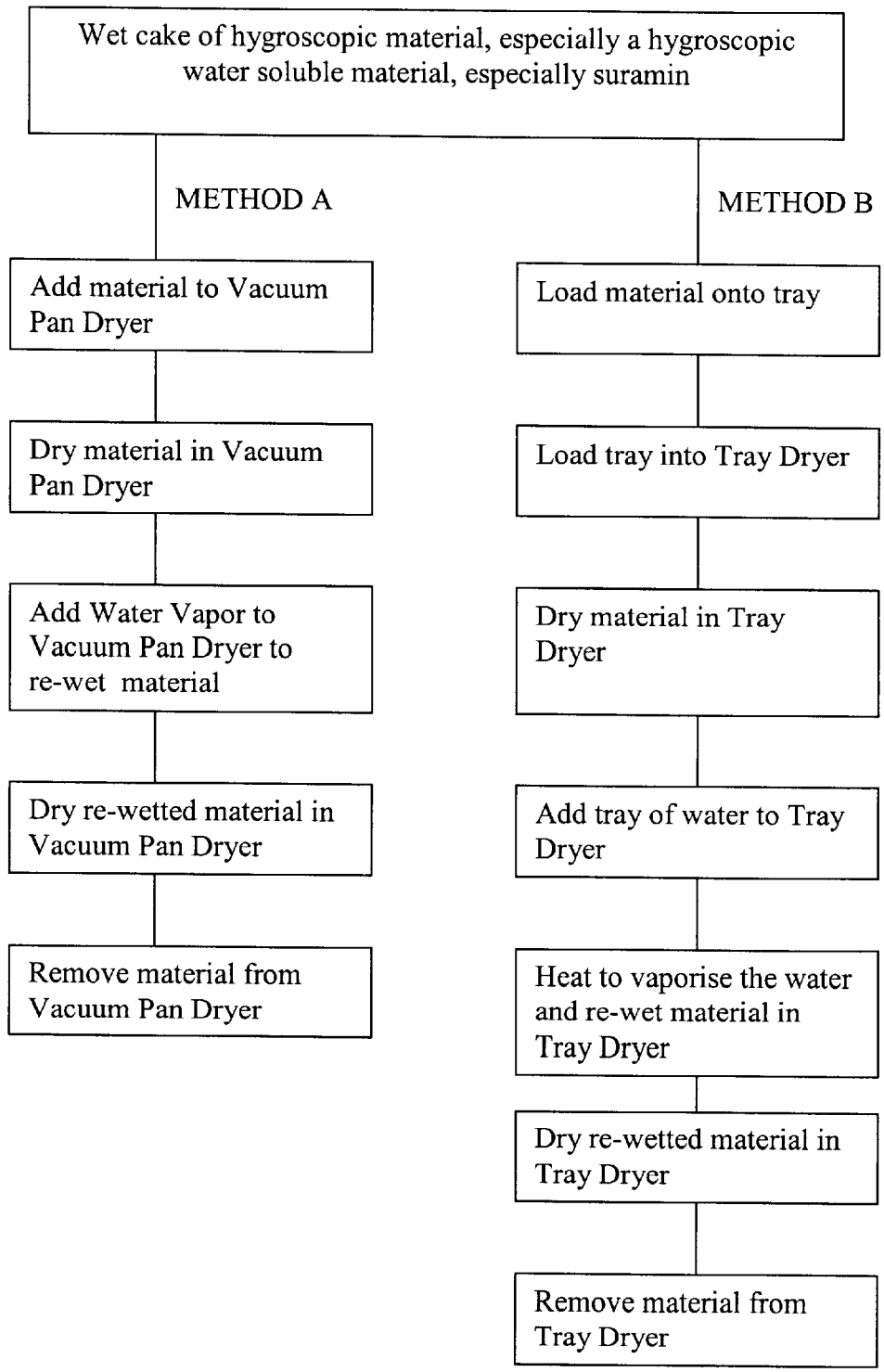

This application is a continuation of the following applications: International application PCT/IE 00/00157 filed Dec. 18, 2000, which claims priority from international application PCT/IE 99/00138 filed Dec. 17, 1999, all of which are incorporated herein by reference in their entirety.

FIELD OF THE INVENTION

The invention relates to a factory scale process for removing trace solvent from a material, especially a hygroscopic material. In particular, the invention relates to an improved process for producing suramin, the hexasodium salt of a polysulfonated naphthylurea, 8,8'-[carbonylbis[imino-3,1-phenylene-carbonylimino (4-methyl-3,1 -phenylene) carbonyl-imino]]bis-1,3,5-naphthalenetrisulfonic acid.

BACKGROUND OF THE INVENTION

Suramin has been utilized clinically since the 1920s as an antiparasitic agent, and more recently has been shown to be active in the treatment of metastatic cancer; Stein et al., J. Clin. Oncology 1989;7(4):499–508. U.S. Pat. Nos. 5,767,110 and 5,597,830 describe the synergistic effect of suramin in combination with a vinca alkaloid or estramustine for treating cancer.

In addition, suramin can be used for treating autoimmune and allergic diseases such as rheumatoid arthritis, Crohn's disease, ulcerative colitis, glomerular nephrites, systemic lupus erythematosus, polymyositis, Sjogren's syndrome, asthma, and other inflammatory alveolar diseases. Suramin can also be used for treating AIDS and human T cell leukaemia virus.

The process for producing suramin is well-known, GB 224.849; however, it was unexpectedly found that on scale up to a commercial factory scale the drying regime of the final product was slow and difficult to optimize so as to obtain the desired finished product. It was found that unacceptable levels of reaction solvents were present in the final product. Similar problems arise in drying other materials, especially hygroscopic materials.

The object of the present invention is therefore to provide an improved process for removing trace solvents from a material, especially a hygroscopic material on a factory scale, which routinely and consistently produces material of a high quality.

SUMMARY OF THE INVENTION

According to the invention there is provided a factory scale process for removing trace solvent from a material comprising the steps of:
(a) providing a dryer;
(b) drying an isolated product in a dryer to remove free solvent;
(c) rewetting the product with water; and
(d) redrying the product to remove residual solvent to the required level.

The process of the invention facilitates the factory scale production of dried product with a very low level of residual solvent. Intermediate milling of the product is not required and drying time is much reduced.

Preferably, the product is rewetted with water vapor. Ideally, the added water is generated from pyrogen controlled deionized water.

In one embodiment of the invention the product is heated to facilitate the rewetting process.

In one embodiment of the invention the product is dried in a vacuum agitated pan dryer. In this case, preferably, the product is rewetted by injecting water vapor into the pan dryer. In a preferred embodiment the process includes the step of intermittently stopping the injection of water vapor into the pan dryer and agitating and sampling the product before recommencing the injection of water vapor. Ideally, the water vapor is injected into the pan dryer using an inert carrier such as nitrogen gas.

In another embodiment the product is dried in a tray dryer. In this case the process includes the steps of:
(a) loading at least one tray containing product into the tray dryer;
(b) loading at least one other tray containing water into the tray dryer; and
(c) heating the water in the dryer to rewet the product.

Preferably, the tray dryer includes a number of dryer cells and a tray containing product and a tray containing water are loaded into a dryer cell. In a preferred embodiment the process includes the steps of removing the water tray prior to drying of the product.

The invention is particularly applicable to hygroscopic materials such as suramin. The term hygroscopic refers to a product which takes up at least some water, for example, by absorption.

The invention also provides for a product whenever produced by a process of the invention. A further embodiment provides suramin whenever produced by a process of the invention.

DETAILED DESCRIPTION OF THE INVENTION

Suramin has the following chemical structure:

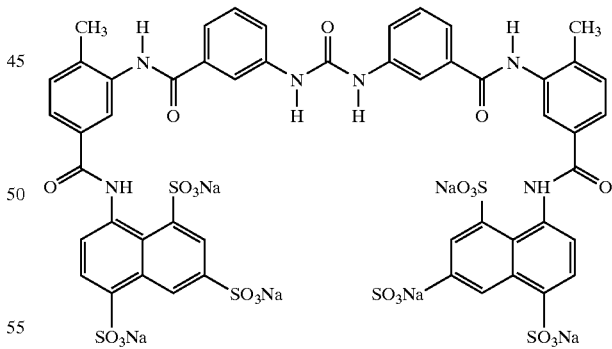

It is a white or slightly pink or cream-coloured powder. It has a slightly bitter taste. It is hygroscopic and is freely soluble in water and in physiological saline.

Suramin is produced from 8-[3-(3-aminobenzamido)-4-methylbenzamido]-1,3,5-napthalenetrisulfonic acid sodium salt in the presence of bistrichloromethylcarbonate (BTCMC)(Triphosgene) and sodium hydroxide as shown in the following reaction scheme.

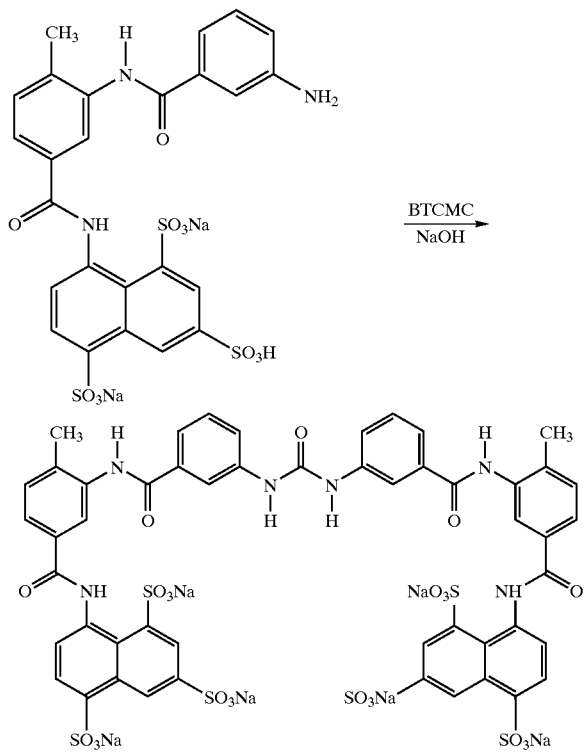

Typical methods for drying the final product involve drying under vacuum for up to 8 days. During the drying procedure the drying is interrupted and the product is milled and sieved before recommencing drying. However, it was found that when this process was scaled up to a commercial factory scale the process resulted in a product with high levels of reaction solvents, such as methanol, still present.

The invention provides an improved drying regime using a vacuum agitated pan dryer or tray dryer. The initial drying procedure reduces the methanol content to 0.3% to 0.8%. The product is then rewetted by passing a stream of steam through the headspace of the dryer. When the water content of the product has increased sufficiently, to 10% to 15%, rewetting is stopped, and the product is redried under vacuum at 80° C. until dry. This procedure allows high quality suramin with a water content of less than 10% and a methanol content of less than 0.1% to be produced on a consistent basis. Intermediate milling of the material is not necessary and the drying time is much reduced.

The invention will be more clearly understood from the following description given by way of example.

EXAMPLE 1

Preparation of Crude Suramin 142 kg 8-[3-(3-Aminobenzamido)-4-methylbenzamido]-1,3,5-napthalenetrisulfonic acid sodium salt prepared by known methods and 1150 liters water are charged to a reaction vessel and agitated for approximately 10 minutes until the solution is dissolved. 2 N hydrochloric acid (71 kg concentrated hydrochloric acid in 284 liters water) is charged to the reaction vessel until the pH is in the range 3.8 to 4.0.

A solution of 17 kg triphosgene and 62 kg toluene are charged to the reaction vessel over approximately 2 hours. The pH is maintained at 3.5 to 4.0 by charging as required with a solution of 2 N sodium hydroxide (21.3 kg sodium hydroxide in 264 kg water) and the temperature maintained at 20° C. to 3° C. After agitation for at least 1 hour, 206 kg toluene is added to the reaction vessel and the contents agitated at 70 rpm for 15 minutes. The contents are allowed to settle and the lower rich aqueous layer is transferred to another vessel. A number of toluene washes of the rich aqueous layer are carried out to remove residual phosgene, and all the waste toluene streams are combined for decontamination before disposal. The pH of the rich aqueous layer is adjusted to 6.0 to 6.5 with 2 N sodium hydroxide and the contents agitated for 15 minutes. A full vacuum is applied to the vessel and the contents distilled at 60° C. until 234 to 248 liters remain. The pH is adjusted to 6.0 to 6.5 using 2 N sodium hydroxide. The contents are then heated to 60° C. to 70° C. and 1005 kg filtered methanol is added. The contents are polish filtered through a single plate, a multiplate sparkler, and multielement cartridge filter.

After filtration, the filtrate is cooled to 34° C. to 36° C. and agitated at 50 to 90 rpm and further cooled at about 1° C./10 minutes until crystallization commences. While cooling, the contents are seeded with 10 g aliquots of suramin seeds. When crystallization begins the contents are agitated for 8 hours without temperature regulation. After 8 hours the contents are agitated at 15° C. to 20° C. for at least 6 hours, the contents are further cooled to −2 to +2° C. and agitated for at least 3 hours. The crude suramin product is centrifuged and discharged to polyethylene lined bins.

EXAMPLE 2

Preparation of Pure Suramin

Wet crude suramin as prepared in Example 1 (corresponding to 138.7 kg estimated dried weight) is charged to a reaction vessel followed by 39 liters pyrogen controlled deionized water and 256.5 kg filtered methanol. The contents are agitated at 50° C. to 60° C. until in solution. The solution is cooled to 55° C. and polish filtered as described in Example 1. The solution is further cooled to 35° C., agitation is reduced to 50 to 90 rpm, and the solution cooled at 1° C./10 minutes. The solution is seeded with suramin seeds until crystallization begins. The contents are agitated for at least 8 hours without temperature regulation. After 8 hours the contents are cooled to 15° C.–20° C. and held at this temperature for at least 6 hours. The solution is then cooled to −2° C.–+2° C. for at least 3 hours. The pure suramin product is then isolated on a centrifuge and dried.

EXAMPLE 3

Drying Suramin
METHOD A (Pan Dryer)

The wet cake product from Example 2 is loaded into a stainless steel agitated jacketed vacuum pan dryer (Guedo mixed dryer type 2500). Slow continuous agitation at 10 rpm is begun, the jacket temperature is increased to 55° C. to 65° C., and the product dried for 6 hours. The jacket temperature is then increased to 75° C. to 85° C. with full vacuum until a water content of less than 9% is achieved.

The temperature of the dryer jacket is adjusted to 70° C. Filtered steam prepared from pyrogen controlled water is injected into the dryer using nitrogen gas as a carrier. The steam injection is stopped and the product agitated for 5 to 10 minutes before sampling. Steaming is then continued until a water content of more than 10% but less than 15% is achieved. Vacuum drying is recommenced and the product is dried at 75° C. to 85° C. until the water content is less than 10% and a methanol content of less than 0.1% is achieved. The product is discharged and packed in moisture resistant bags. The drying time usually takes less than 2 days.

METHOD B (Tray Dryer)

The wet cake product from Example 2 is loaded onto trays in a stainless steel tray dryer (William Boulton Model C3) by evenly spreading the product on the trays. The product is dried at a jacket temperature of approximately 35° C. to 45° C. with full vacuum for a minimum of 12 hours. The jacket temperature is increased to 45° C. to 75° C. and the product dried for a minimum of 6 hours until a water content of less than 9% is achieved.

One tray of product along with a tray of pyrogen controlled deionised water is loaded into each of the dryer cells. The dryer is heated to 70° C. until the water content in the cake is between 10% and 15%. The water trays are then removed and the product trays heated to 80° C. and dried under vacuum until a water content of less than 10% and a methanol content of less than 0.1% is achieved. The product is discharged and packed in moisture resistant bags.

While the invention has been described with reference to the factory scale production of suramin, it is anticipated that it will also be applicable to other materials, especially hygroscopic materials.

The invention is not limited to the embodiments hereinbefore described which may be varied in detail.

What is claimed is:

1. A factory scale process for removing trace solvent from a hygroscopic material comprising the steps of:
   (a) providing a dryer;
   (b) drying an isolated product in the dryer to remove free solvent;
   (c) rewetting the product with water; and
   (d) redrying the product to remove residual solvent.

2. A process as claimed in claim 1 comprising rewetting the product with water vapor.

3. A process as claimed in claim 1 comprising generating the added water from pyrogen controlled deionized water.

4. A process as claimed in claim 1 comprising generating the added water in the same chamber as the product being dried.

5. A process as claimed in claim 1 wherein the dryer is a vacuum agitated pan dryer.

6. A process as claimed in claim 5 comprising rewetting the product by injecting water vapor into the pan dryer.

7. A process as claimed in claim 6 comprising intermittently stopping the injection of water vapor into the pan dryer, agitating the product, and sampling the product before recommencing the injection of water vapor.

8. A process as claimed in claim 6 comprising injecting the water vapor into the pan dryer using an inert carrier.

9. A process as claimed in claim 1 wherein the dryer is a tray dryer.

10. A process as claimed in claim 9 wherein the process comprises the steps of:
    (a) loading at least one tray containing product into the tray dryer;
    (b) loading at least one other tray containing water into the tray dryer; and
    (c) heating the water in the dryer to rewet the product.

11. A process as claimed in claim 10 wherein the tray dryer includes a number of dryer cells and the process comprises loading a tray containing product into a dryer cell and loading a tray containing water into the same dryer cell.

12. A process as claimed in claim 11 comprising removing the water tray prior to drying of the product.

13. A factory scale process for removing trace solvent from a hygroscopic water soluble material comprising the steps of:
    (a) providing a dryer;
    (b) drying an isolated product in a dryer to remove free solvent;
    (c) rewetting the product with water; and
    (d) redrying the product to remove residual solvent.

14. A process as claimed in claim 13 comprising rewetting the product with water vapor.

15. A process as claimed in claim 13 comprising generating the added water from pyrogen controlled deionized water.

16. A process as claimed in claim 13 comprising generating the added water in the same chamber as the product being dried.

17. A process as claimed in claim 13 wherein the dryer is a vacuum agitated pan dryer.

18. A process as claimed in claim 17 comprising rewetting the product by injecting water vapor into the pan dryer.

19. A process as claimed in claim 18 comprising intermittently stopping the injection of water vapor into the pan dryer, agitating the product, and sampling the product before recommencing the injection of water vapor.

20. A process as claimed in claim 18 comprising injecting the water vapor into the pan dryer using an inert carrier.

21. A process as claimed in claim 13 wherein the dryer is a tray dryer.

22. A process as claimed in claim 21 wherein the process comprises the steps of:
    (a) loading at least one tray containing product into the tray dryer;
    (b) loading at least one other tray containing water into the tray dryer; and
    (c) heating the water in the dryer to rewet the product.

23. A process as claimed in claim 22 wherein the tray dryer includes a number of dryer cells and the process comprises loading a tray containing product into a dryer cell and loading a tray containing water into the same dryer cell.

24. A process as claimed in claim 23 comprising removing the water tray prior to drying of the product.

25. A factory scale process for removing trace solvent from suramin comprising the steps of:
    (a) providing a dryer;
    (b) drying an isolated suramin product in a dryer to remove free solvent;
    (c) rewetting the product with water; and
    (d) redrying the product to remove residual solvent.

26. A process as claimed in claim 25 comprising rewetting the product with water vapor.

27. A process as claimed in claim 25 comprising generating the added water from pyrogen controlled deionized water.

28. A process as claimed in claim 25 comprising generating the added water in the same chamber as the product being dried.

29. A process as claimed in claim 25 wherein the dryer is a vacuum agitated pan dryer.

30. A process as claimed in claim 29 comprising rewetting the product by injecting water vapor into the pan dryer.

31. A process as claimed in claim 30 comprising intermittently stopping the injection of water vapor into the pan dryer, agitating the product, and sampling the product before recommencing the injection of water vapor.

32. A process as claimed in claim 25 comprising injecting the water vapor into the pan dryer using an inert carrier.

33. A process as claimed in claim 25 wherein the dryer is a tray dryer.

34. A process as claimed in claim 33 wherein the process comprises the steps of:
   (a) loading at least one tray containing product into the tray dryer;
   (b) loading at least one other tray containing water into the tray dryer; and
   (c) heating the water in the dryer to rewet the product.

35. A process as claimed in claim 34 wherein the tray dryer includes a number of dryer cells and the process comprises loading a tray containing product into a dryer cell and loading a tray containing water into the same dryer cell.

36. A process as claimed in claim 35 comprising removing the water tray prior to drying of the product.

* * * * *